US011833340B2

(12) United States Patent
Born

(10) Patent No.: US 11,833,340 B2
(45) Date of Patent: Dec. 5, 2023

(54) SYRINGE AND PLUNGER CLIP FOR BOTTLES

(71) Applicant: Jennifer Anne Born, Hannibal, MO (US)

(72) Inventor: Jennifer Anne Born, Hannibal, MO (US)

(73) Assignee: Born Life Hacks, LLC, Hannibal, MO (US)

( * ) Notice: Subject to any disclaimer, the term of this patent is extended or adjusted under 35 U.S.C. 154(b) by 336 days.

(21) Appl. No.: 17/126,515

(22) Filed: Dec. 18, 2020

(65) Prior Publication Data

US 2021/0100962 A1   Apr. 8, 2021

Related U.S. Application Data

(63) Continuation-in-part of application No. 16/286,824, filed on Feb. 27, 2019, now Pat. No. 10,898,411.

(51) Int. Cl.
*A61M 5/52* (2006.01)
*A61J 1/16* (2023.01)

(52) U.S. Cl.
CPC .............. *A61M 5/52* (2013.01); *A61J 1/16* (2013.01); *A61M 2209/082* (2013.01)

(58) Field of Classification Search
CPC ....... A61M 5/52; A61M 2209/082; A61J 1/16
See application file for complete search history.

(56) References Cited

U.S. PATENT DOCUMENTS

| 2,949,203 | A | * | 8/1960 | Henry | A61J 1/05 |
| | | | | | D24/117 |
| 3,066,361 | A | * | 12/1962 | England | A61M 5/001 |
| | | | | | 206/365 |
| 5,005,793 | A | * | 4/1991 | Shillington | A61M 5/1418 |
| | | | | | 248/912 |
| D363,211 | S | | 10/1995 | Noble | |
| 6,244,554 | B1 | * | 6/2001 | Baker | A47F 7/28 |
| | | | | | 215/396 |
| 6,565,054 | B2 | | 5/2003 | Weesner | |
| 7,959,122 | B1 | * | 6/2011 | Clack-Hopkins | A61M 5/1417 |
| | | | | | 248/315 |
| 8,550,418 | B2 | * | 10/2013 | Gesler, III | A61M 5/008 |
| | | | | | 211/85.13 |
| 10,064,510 | B1 | * | 9/2018 | Yablon | A47G 23/0208 |
| 10,500,343 | B2 | * | 12/2019 | Poulos | A61M 5/31533 |
| 10,722,432 | B2 | * | 7/2020 | Davis | A61M 5/31513 |
| D978,636 | S | * | 2/2023 | Valdez-Santos | D7/701 |
| 2009/0254030 | A1 | | 10/2009 | Sarraf | |

FOREIGN PATENT DOCUMENTS

EP   1306313 A1   5/2003

* cited by examiner

*Primary Examiner* — Anita M King

(57) ABSTRACT

One embodiment of a mechanism for attaching a syringe and separated plunger to a bottle and of the type having an attachment member (110) from which restraints (114) extend. In being fastened to the bottle, the restraints enable convenient drying and storage of the syringe and the separated plunger. Other embodiments are described and shown.

9 Claims, 6 Drawing Sheets

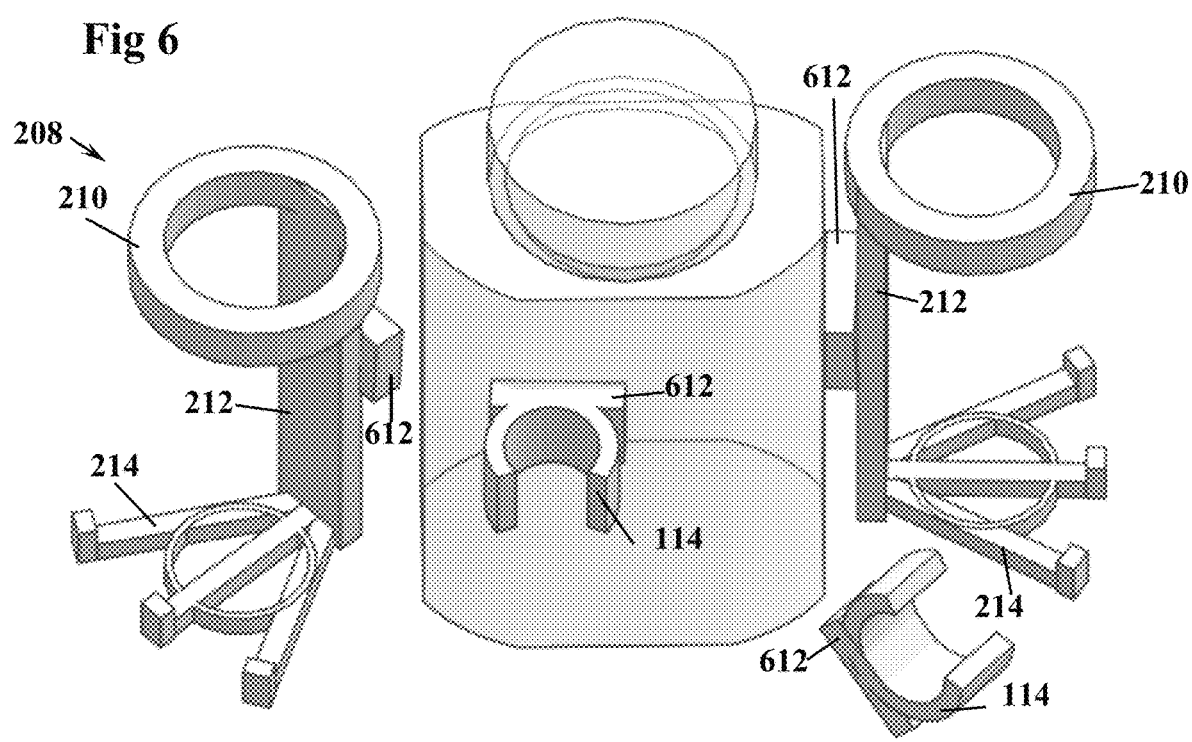

SYRINGE AND PLUNGER CLIP FOR BOTTLES

CROSS-REFERENCE TO RELATED APPLICATIONS

This application claims priority to U.S. application Ser. No. 16/286,824. filed on Feb. 27, 2019, which claims priority to U.S. Provisional Application No. 62/636,926, filed Mar. 1, 2018, by the present inventor, which is incorporated by reference in its entirety.

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OF A JOINT INVENTOR

Not Applicable

BACKGROUND OF THE INVENTION

Companies that produce over-the-counter liquid medicines commonly supply reusable syringes and separated plungers with their products, as do pharmacies which fill liquid medicine prescriptions. When dispensing these medicines, it is critical to give the recipient, often infants, the correct dosage down to the milliliter, which is why consumers are provided with syringes marked with detailed measurements. In my experience, it is important that users be able to store these dispensing items with the medicine to provide the highest level of care and safety. In addition, it is necessary that users be able to locate these dispensing items. Thus, the optimal solution is to store the dispensing items attached to the bottle itself. The syringes and separated plungers are intended to be washed after each use to remove remaining traces of medicine and bacteria from dispensing to the recipient. After washing the dispensing items, I have found that the user lacks a convenient and hygienic option for drying the syringe and separated plunger. This lacking leads the user to utilizing counter tops, sinks, paper towels, plates, washcloths, or other inconvenient and unsanitary means for drying. Once the syringe and separated plunger are dry, the user must store the items. The resulting situation leaves the user with only similarly deficient storage options: the opened box in which the medicine was sold, a resealable plastic bag, a bathroom drawer with various other items, or placed haphazardly near the bottle.

BACKGROUND—PRIOR ART

The following is a tabulation of some prior art that presently appears relevant:

| U.S. Patents | | | |
|---|---|---|---|
| Pat. No. | Kind Code | Issue Date | Patentee |
| 6,565,054 | B2 | 2003 May 20 | Weesner |
| 363,211 | S | 1995 Oct. 17 | Noble |
| 20090254030 | A1 | 2009 Oct. 08 | Sarraf |

| Foreign Patents | | | |
|---|---|---|---|
| Pat. No. | Kind Code | Issue Date | Patentee |
| EP1306313 | A1 | 2003 May 02 | Gerner |

Weesner discloses a complex attachment for a syringe, but provides a single restraint for a traditional syringe containing a needle. The attachment mechanism is ineffective for multiple reasons including the short shelf life of elasticity and the limited number of restraints. Sarraf discloses a combination bottle, clip, and syringe which is ineffective because most liquid medicine companies and pharmacies use cylindrical bottles instead of Sarraf's patented bottle. Noble discloses a mortised ring attachment, but provides a single restraint for a traditional syringe containing a needle. Gerner discloses a device that attaches a single ampule to a traditional syringe containing a needle, but does not provide attachment for the syringe to a larger medicine bottle.

BRIEF SUMMARY

In accordance with one embodiment, a syringe and plunger clip comprises an attachment that secures a plurality of restraints to a bottle to provide hygienic drying and storage. The clip solves the above-discussed problems and obtains advantages not previously possible.
Advantages
Accordingly, several advantages of one or more aspects are as follows. One or more aspects provide an attachment mechanism that enables convenient storage of a syringe and separated plunger without utilizing counters, plates, napkins, paper towels, etc. The clip enables hygienic drying of a syringe and separated plunger after washing those items while being stored in combination with the bottle. Being able to conveniently and hygienically dry the separated syringe and plunger with the medicine bottle provides parents and caregivers with an innovative solution. The clip allows for attachment to a non-proprietary, typical medicine bottle. The clip is relatively inexpensive. The clip prevents misplacing the syringe and separated plunger, and thereby provides a tidy and hygienic solution minimizing frustration for users dispensing liquid medicine. The clip allows users to prevent cross contamination from medicine recipients. The clip is itself washable and sanitizable.

BRIEF DESCRIPTION OF DRAWINGS

In the drawings, closely related figures have the same number, but different alphabetic suffixes.

FIG. 1C' shows a front perspective view of similar attachment member as an openable ring, an adjustable ring, or an openable and adjustable ring in opened position, in accordance with another embodiment.

FIG. 6 shows a top perspective view having various combinations of restraints and arms, in accordance with other embodiments.

Figure 1:
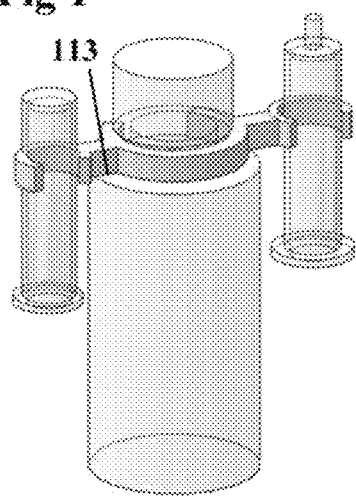
FIG. 1 shows a perspective view with an example bottle, syringe, and separated plunger, in accordance with one embodiment.

The bottle, syringe, and plunger in the included figures are for illustrative purposes only and do not form part of the claimed design.

| Drawings - Reference Numerals | | | |
|---|---|---|---|
| 110 | Cutout Ring Attachment Member | 122 | Interlocking Arm Protrusion |
| 110a | Cutout Opening of Attachment Member | 124 | Interlocking Arm Receptacle |
| 110b | Gripping Points of Attachment Member | 208 | Holster Restraint |
| 110c | Hole in Attachment Member | 210 | Restraint Upper Ring |
| 112 | Solid Arm | 212 | Stem |
| 113 | Weight-Bearing Juncture of Assembly and Bottle | 214 | Restraint Lower Base |
| | | 214a | Appendages |
| 114 | Cutout Ring Restraint | 214b | Circular Support Structure |
| 114a | Cutout Section of Ring Restraint | 214c | Endcap |
| 114b | Gripping Points of Ring Restraint | 310 | Open Band Attachment Member |
| 114c | Hole in Restraint | 312 | Band Enclosure |
| 117 | Fully-enclosed Ring Attachment Member | 314 | Band Arm |
| | | 316 | Fully-enclosed Band Attachment Member |
| 118 | Openable Ring Attachment Member | | |
| 120 | Interlocking Arm | 612 | Direct Attachment Arms |

DETAILED DESCRIPTION OF THE INVENTION

Thus, some embodiments provide a clip that attaches a syringe and separated plunger to a bottle thereby enabling hygienic and convenient drying and storage unlike prior-art mechanisms. Some embodiments provide a mechanism that enables attachment to differently-sized bottles and for differently-sized syringes and separated plungers unlike prior-art mechanisms. These benefits and others of one or more aspects will become apparent from a consideration of the ensuing description and accompanying drawings.

Figure 1A:
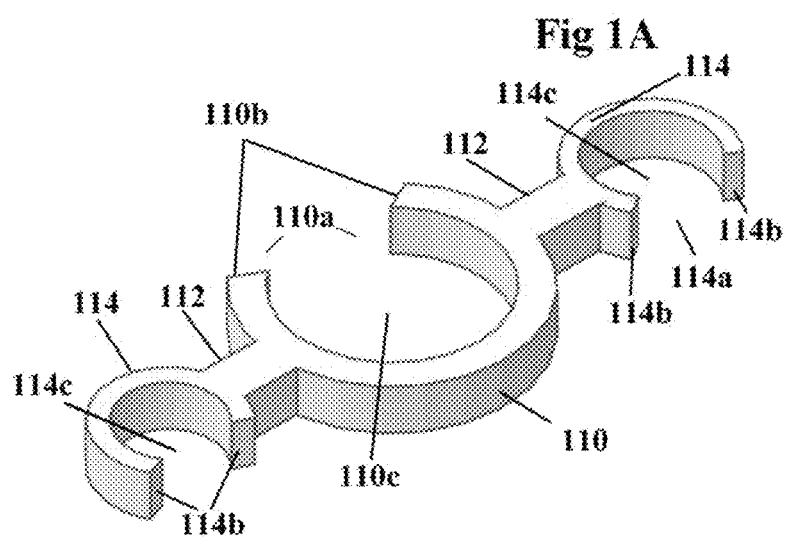
FIG. 1A shows a perspective view with the attachment member as a cutout ring and restraints as cutout rings and solid joining arms, in accordance with one embodiment.
Figure 1B:
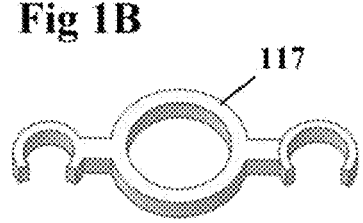
FIG. 1B shows a front perspective view of a similar attachment member as a fully-enclosed ring, in accordance with another embodiment.

Description—First Embodiment (FIGS. 1-1A):

One embodiment of the clip is illustrated in FIGS. 1 and 1A (perspective view) and FIG. 1A (plan view). The embodiment has an attachment member 110 comprising a ring with a cutout opening 110a. From the attachment member, a plurality of solid arms 112 extend in diverging directions contiguously for sufficient distance to provide clearance between a bottle and a syringe and a separated plunger. The solid arms terminate in restraints 114. The restraints are comprised of rings with cutouts 114a. In one embodiment, the clip is plastic, however the clip can be made of any material that can provide firm, but reasonably flexible attachments for the syringe and the separated plunger. The clip rests its weight upon the shoulder of the bottle, lower adjacent to the bottle's neck 113. The attachment member, arms, and restraints are joined intrinsically as a result of 3D printing or injection molding in one embodiment. However, these components may also be formed separately and joined with adhesive, hardware connections such as screws or nails, welding or soldering metal components, or another suitable method.

Operation—First Embodiment (FIGS. 1-1A):

To use the clip, hold it so that the plane of the clip is generally perpendicular to the axis of the bottle and cutout opening 110a is adjacent to the bottle's neck. Press the cutout opening of the attachment member onto the bottle's neck until it is forced past gripping points 110b and into the hole, securing the clip to the bottle's neck. Press the barrel of the syringe into the cutout of one of the restraints perpendicularly, past the restraint's gripping points 114b and into the hole. Press the barrel of the separated plunger into the cutout of another of the restraints perpendicularly, past the restraint's gripping points and into the hole. These steps can be performed in any order. The clip will now hold the syringe and the separated plunger attached to the bottle, allowing them to dry and providing convenient storage.

To remove the syringe and the separated plunger from the clip, pull them from the clip through the restraint's cutout, past the gripping points and out of the hole with sufficient force to release them. To remove the clip from the bottle, exert sufficient force on the clip in the opposite direction of its cutout while also restraining the bottle.

The clip can be used repeatedly. It can be detached from one bottle once empty and attached to a new bottle. The syringe and plunger stay attached to the bottle for convenient storage and are clean and dry for the next use. No additional waste or mess is created.

Description—Additional Embodiment (FIGS. 2, 2A-D):

FIGS. 2 and 2A-D show an additional embodiment. The embodiment has an attachment member 110 comprising a ring with a cutout opening. From the attachment member, a plurality of solid arms 112 extend in diverging directions contiguously for sufficient distance to provide clearance between a bottle and a syringe and a separated plunger. The arms join attachment member 110 to a restraint upper ring 210. Restraint upper ring 210 is comprised of a ring. Restraint upper ring 210 is joined perpendicularly to a stem 212 on the upper vertical end of stem 212. Stem 212 is joined on the lower vertical end to a restraint lower base 214. Stem 212 is joined perpendicularly to restraint upper ring 210 at a right angle to the underside or backside of restraint upper ring 210. Stem 212 is joined perpendicularly to restraint lower base 214 at a right angle to the topside or backside of the restraint lower base 214. The combination of restraint upper ring 210, stem 212, and restraint lower base 214 forms a holster restraint 208 for storing and drying the syringe and the separated plunger.

Restraint lower base 214, in this embodiment, comprises a plurality of appendages 214a extending in diverging directions from the lower end of stem 212 and terminating in a plurality of endcaps 214c, with a circular support structure 214b intersecting the plurality of appendages. Other restraint lower bases of various shapes and designs that restrain the syringe and the separated plunger substantially and facilitate adequate drying would be suitable.

The aforementioned components in this embodiment are joined intrinsically as a result of 3D printing or injection molding. However, these components may also be formed separately and joined with adhesive, hardware connections such as screws or nails, welding or soldering metal components, or another suitable method.

Operation—Additional Embodiment (FIGS. 2, 2A-D):

To use the clip, hold the clip so that its upper plane is generally perpendicular to the axis of the bottle and cutout opening is adjacent to the bottle's neck. Press the cutout of the attachment member onto the bottle's neck until it is forced past gripping points on the attachment member and into the hole, securing the clip to the bottle. Insert the syringe and the separated plunger into the restraints respectively in one of two ways: 1) lower the syringe and the separated plunger through the restraint upper ring to rest on the restraint lower base, or 2) angle and lift the syringe and the separated plunger up into the void in the restraint upper ring, then lower to rest on the restraint lower base. These steps can be performed in any order individually for the syringe and the separated plunger.

To remove, lift the syringe and the separated plunger farther into the restraint upper ring off the restraint lower base, angle the syringe and the separated plunger out away from the back of the embodiment, and lower the syringe and the separated plunger out of the restraint upper ring. To remove the embodiment from the bottle, exert sufficient force on the embodiment in the opposite direction of its cutout while also restraining the bottle.

Description—Additional Embodiment (FIGS. 3, 3A-C):

FIGS. 3 and 3A-C show an additional embodiment. This embodiment comprises an open band attachment member 310, a plurality of band enclosures 312, a plurality of restraints 114, and a plurality of band arms 314. The open band attachment member comprises an oval band. The open band is not fully-enclosed, but rather terminates in band enclosures 312. The plurality of restraints are comprised of rings with cutouts. The plurality of restraints are joined to the open band by band arms 314. Alternatively, the restraints could be joined to the open band directly during the manufacturing process.

The aforementioned components in this embodiment are joined intrinsically as a result of 3D printing or injection molding. However, these components may also be formed separately and joined with adhesive, hardware connections such as screws or nails, welding or soldering metal components, or another suitable method.

Operation—Additional Embodiment (FIGS. 3, 3A-C):

To use the clip, slide the void of open band 310 down over or up under the bottle to attach to the bottle's body. Press the barrel of the syringe into the cutout opening of one of the restraints perpendicularly, past the restraint's gripping points and into the hole. Then, press the barrel of the separated plunger into the cutout of another one of the restraints perpendicularly, past the restraint's gripping points and into the hole. Thus, the syringe and the separated plunger are secured to the open band and, therefore, to the bottle. These steps can be performed in any order.

To remove the syringe and the separated plunger from the embodiment, pull them from the restraints on the open band, past the gripping points and out of the hole with sufficient force to release them. To remove the embodiment from the bottle, slide the embodiment off the bottle's body by raising or lowering it off the bottle.

Figure 3:
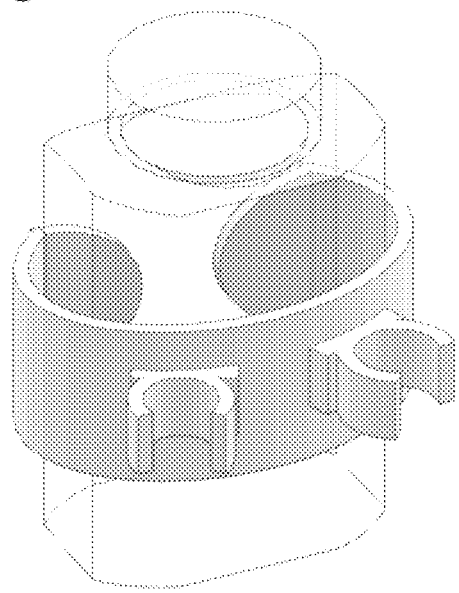
FIG. 3 shows a perspective view of a similar attachment member with an example bottle, syringe, and separated plunger with the attachment member as an open band and restraints as cutout rings and solid joining arms, in accordance with another embodiment.
Figure 3A:
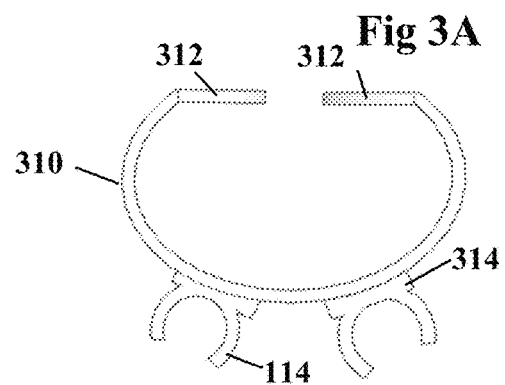
FIGS. 3A-C show various views with the attachment member as an open band, restraints as cutout rings, and solid joining arms, in accordance with another embodiment.
Figure 3B:
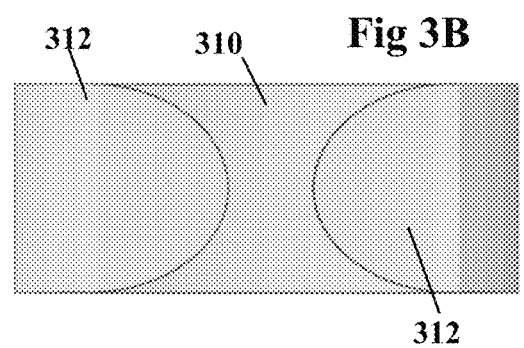
Figure 3C:
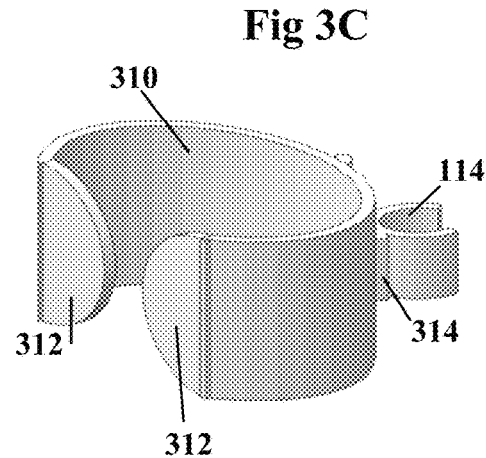
Figure 3D:
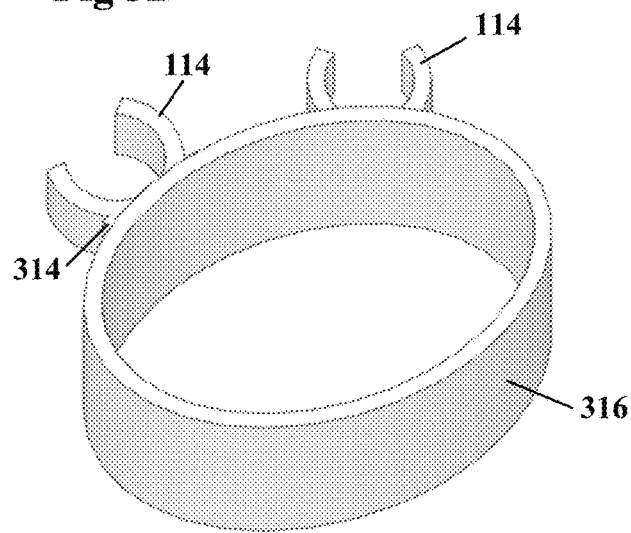
FIG. 3D shows a back perspective view of a similar attachment member with the attachment member as a fully-enclosed band, restraints as cutout rings, and solid joining arms, in accordance with another embodiment.

Description—Additional Embodiment (FIG. 3D):

FIG. 3D shows an additional embodiment. The embodiment comprises a fully-enclosed band attachment member 316, a plurality of restraints 114, and a plurality of band arms 314. The fully-enclosed band attachment member comprises an oval band. The restraints are comprised of rings with cutouts. Restraints 114 are joined to band 316 by band arms 314. Alternatively, restraints 114 could be joined to band 316 directly during the manufacturing process.

The aforementioned components in this embodiment are joined intrinsically as a result of 3D printing or injection molding. However, these components may also be formed separately and joined with adhesive, hardware connections such as screws or nails, welding or soldering metal components, or another suitable method.

Operation—Additional Embodiment (FIG. 3D):

To use the embodiment, slide the void of the band down over or up under the bottle to attach to the bottle's body. Press the barrel of the syringe into the cutout of one of the restraints perpendicularly, past the restraint's gripping points and into the hole. Press the barrel of the separated plunger into the cutout of another one of the restraints perpendicularly, past the restraint's gripping points and into the hole. Thus, the syringe and the separated plunger are secured to the band and, therefore, to the bottle. These steps can be performed in any order.

To remove the syringe and the separated plunger from the embodiment, pull them from the restraints on the band, past the gripping points and out of the hole with sufficient force to release them. To remove the embodiment from the bottle, slide the embodiment off the bottle's body by raising or lowering it off the bottle.

Figure 1C:
FIG. 1C shows a front perspective view of similar attachment member as an openable ring, an adjustable ring, or an openable and adjustable ring in closed position, in accordance with another embodiment.
Figure 1C:
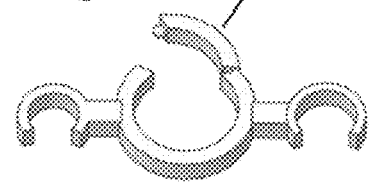
Figure 1D:
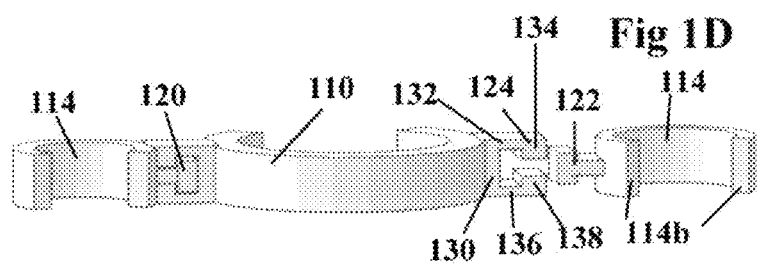
FIGS. 1D-F show various views of similar arms with the ability to detach and interlock, in accordance with another embodiment.

Description—Additional Embodiment (FIGS. 1C-D):

FIGS. 1C-D show additional embodiments comprising a fully-enclosed ring attachment member 117 or an openable ring attachment member 118.

The fully-enclosed ring attachment member is comprised of a fully-enclosed ring.

The openable ring attachment member is comprised of a ring with an openable, an adjustable, or an openable and adjustable enclosure. The openable ring attachment member may include a ring openable with a hinge, a ring with a belt structure, a ring with a ratcheting enclosure apparatus, a clamp, or any suitable enclosure.

Operation—Additional Embodiment (1C-D):

To use the embodiment in FIG. 1C, fit the fully-enclosed ring attachment member over the cap, mouth, and neck of the bottle before inserting the syringe and the separated plunger into the respective restraints. These steps can be performed in any order. To use the embodiment in FIG. 1D, open the enclosure, press the openable ring attachment member onto the neck of the bottle, and fasten the enclosure before inserting the syringe and the separated plunger into the respective restraints. These steps can be performed in any order.

To remove the embodiment in FIG. 1C, lift the fully-enclosed ring attachment member from the cap, mouth, and neck of the bottle and remove the syringe and the separated plunger. To remove the embodiment in FIG. 1D, unfasten the enclosure of the openable ring attachment member from around the bottle and remove the syringe and the separated plunger.

Figure 1E:
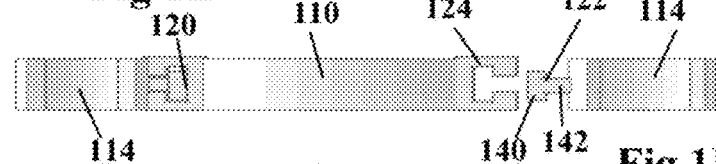
Figure 1F:
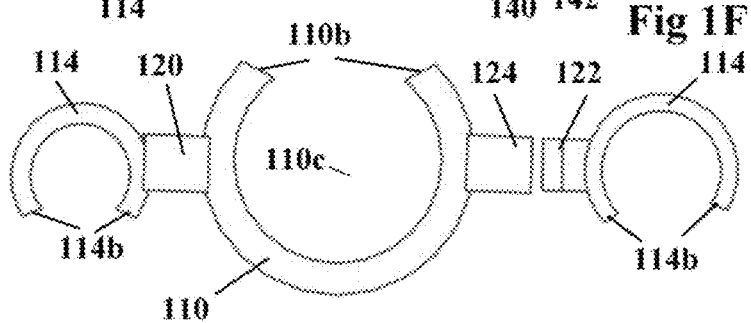
Figure 2:
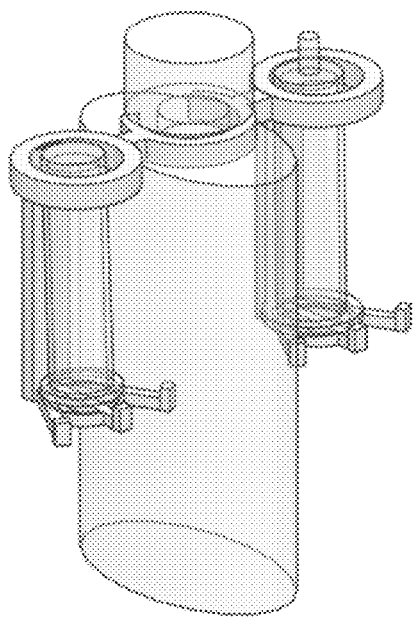
FIG. 2 shows a perspective view with an example bottle, syringe, and separated plunger with the attachment member as a ring with a cutout opening, solid arms and restraints, each as a holster, that is, a restraint upper ring and a restraint lower base connected by a perpendicular stem, in accordance with another embodiment.
Figure 2A:
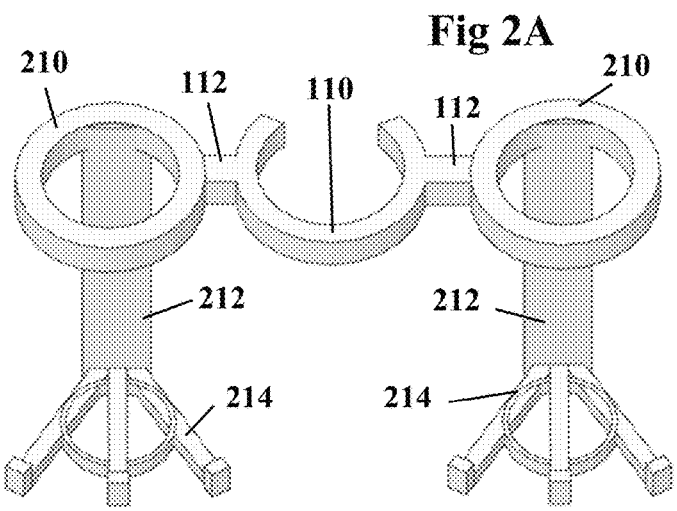
FIGS. 2A-D show various views with the attachment member as a ring with a cutout opening, solid arms and restraints, each as a holster, that is, a restraint upper ring and a restraint lower base connected by a perpendicular stem, in accordance with another embodiment.
Figure 2B:
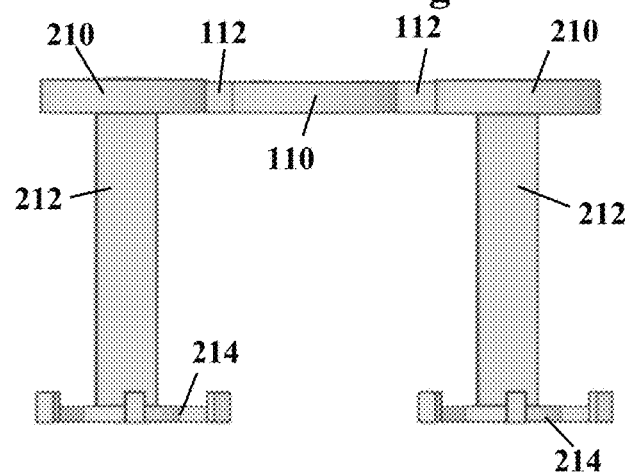
Figure 2C:
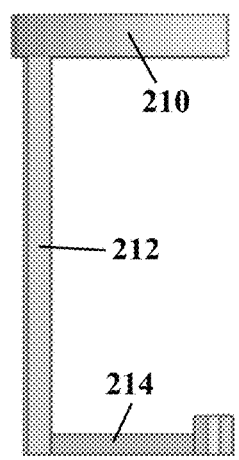
Figure 2D:
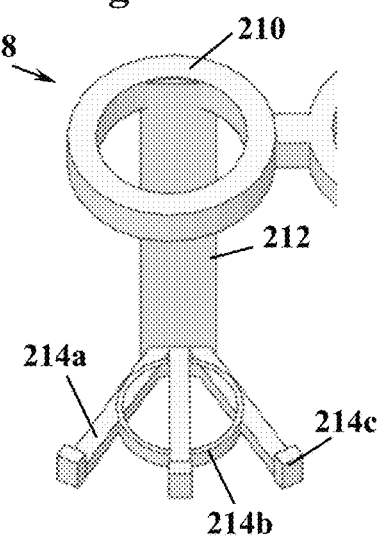

Description—Additional Embodiment (FIGS. 1D-F):

FIGS. 1D-F show an additional embodiment. A plurality of interlocking arms 120 joins an attachment member 110 and a plurality of restraints 114. Each of the interlocking arms is comprised of an interlocking receptacle 124 extending contiguously from the attachment member and an interlocking protrusion 122 extending contiguously from the restraint proximal to the attachment member. Each interlocking receptacle 124 may be comprised of a back vertical portion 130, a top horizontal portion 132 that extends down into a vertical lip 134, a bottom horizontal portion 136 that extends up into a vertical lip 138, wherein the top vertical lip 134 and bottom vertical lip 138 portions are separated. Each interlocking protrusion 122 may be comprised of an outwardly horizontal portion 142 and a vertical perpendicular portion 140.

The aforementioned components in this embodiment are joined intrinsically as a result of 3D printing or injection molding. However, these components may also be formed separately and joined with adhesive, hardware connections such as screws or nails, welding or soldering metal components, or another suitable method. Interlocking receptacle 124 and interlocking protrusion 122 may also be formed separately from attachment member 110 and restraint 114, and joined with adhesive, hardware connections such as screws or nails, welding or soldering metal components, or another suitable method.

Another possible coupling mechanism of the embodiment may be complementary male and female threading devices or another suitable means included in the structures of attachment member 110 and restraints 114.

Operation—Additional Embodiment (FIGS. 1D-F):

To use the embodiment, the user holds one of the restraints and the attachment member with the interlocking receptacle and the interlocking protrusion adjacent. Then, slide the interlocking receptacle and the interlocking protrusion together, engaging the complimentary shapes to fit together, securing the attachment member to one of the restraints fixedly.

The interlocking receptacle and interlocking protrusion may also be switched to be fixed onto the restraints and the attachment member respectively; the substantial matter is that components of the interlocking arms be arranged to enable modular attachment and detachment of the restraints to and from the attachment member for greater user functionality.

Figure 4A:
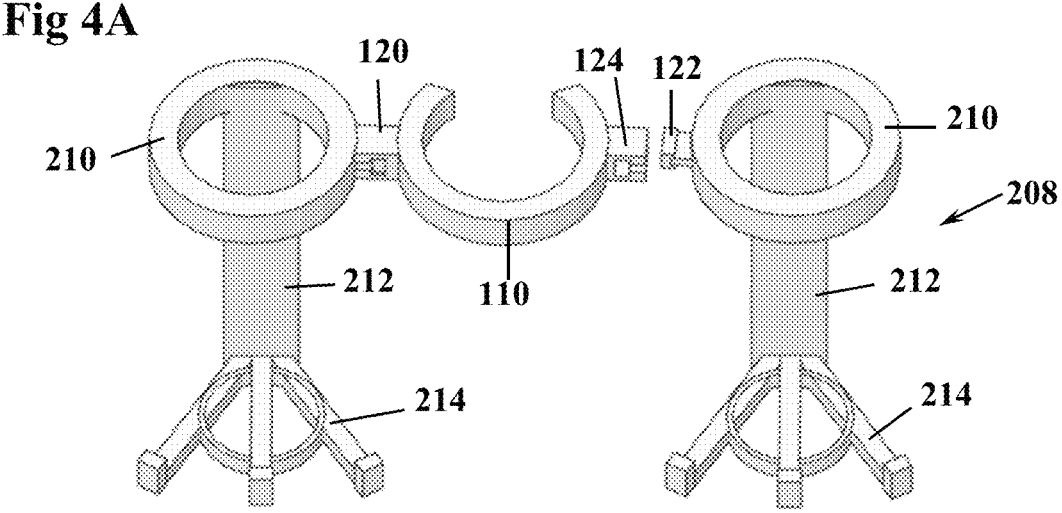
FIGS. 4A-C show various views with the attachment member as a cutout ring, and restraints, each as a holster, that is, a restraint upper ring and a restraint lower base connected by a perpendicular stem, and similar arms to join the attachment member and restraints with the ability to detach and interlock, in accordance with another embodiment.
Figure 4B:
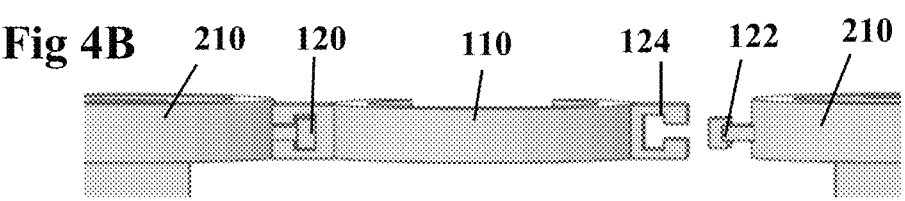
Figure 4C:
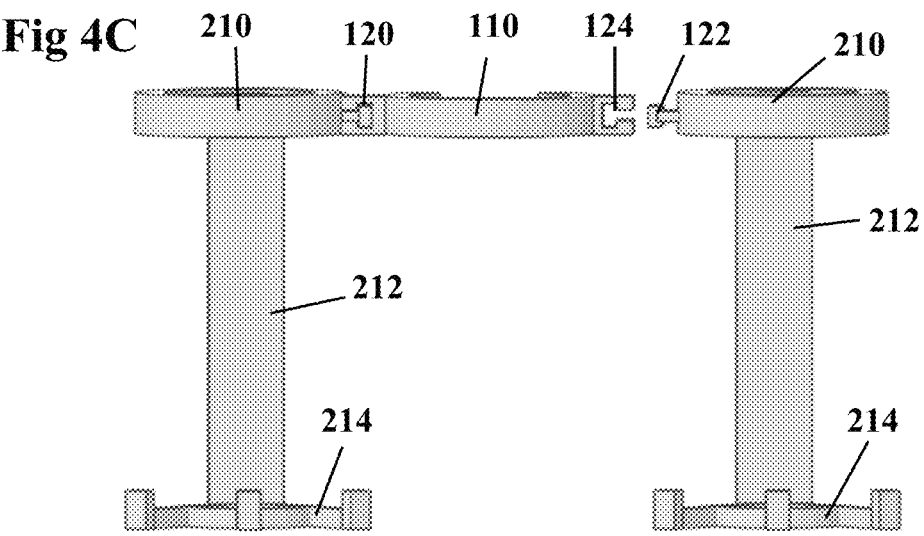

Description—Additional Embodiment (FIGS. 4A-C):

FIGS. 4A-C show an additional embodiment. A plurality of interlocking arms 120 joins an attachment member 110 and holster restraints 208. Each of the interlocking arms is comprised of an interlocking receptacle 124 extending contiguously from attachment member 110 and an interlocking protrusion 122 extending contiguously from a restraint upper ring 210 of one of the holster restraints proximal to the attachment member. Each interlocking receptacle 124 may be comprised of a back vertical portion 130, a top horizontal portion 132 that extends down into a vertical lip 134, a bottom horizontal portion 136 that extends up into a vertical lip 138, wherein the top vertical lip 134 and bottom vertical lip 138 portions are separated. Each interlocking protrusion 122 may be comprised of an outwardly horizontal portion 142 and a vertical perpendicular portion 140.

Attachment member 110 and interlocking receptacle 124, and holster restraints 208 and interlocking protrusion 122 are joined intrinsically as a result of 3D printing or injection molding in one embodiment. However, these components may also be formed separately and joined with adhesive, hardware connections such as screws or nails, welding or soldering metal components, or another suitable method. The interlocking receptacle and the interlocking protrusion may also be formed separately from the attachment member and the restraints, and joined with adhesive, hardware connections such as screws or nails, welding or soldering metal components, or another suitable method.

Another possible coupling mechanism of the embodiment may be complementary male and female threading devices or another suitable means included in the structures of attachment member 110 and holster restraints 208.

Operation—Additional Embodiment (FIGS. 4A-C):

To use the embodiment, hold one of the holster restraints and the attachment member with the interlocking receptacle and the interlocking protrusion adjacent. Then, slide the interlocking receptacle and the interlocking protrusion together, engaging the complimentary shapes to fit together, securing the attachment member to one of the restraints fixedly.

The interlocking receptacle and interlocking protrusion may also be switched to be fixed onto the holster restraints and the attachment member respectively; the substantial matter is that components of interlocking arms 120 be arranged to enable modular attachment and detachment of holster restraints 208 to and from attachment member 110 for greater user functionality.

Figure 5A:
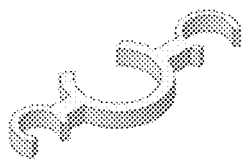
FIG. 5A shows a perspective view with the attachment member as a ring with a cutout opening, solid arms, and restraints as rings with cutout openings, in accordance with one embodiment.
Figure 5B:
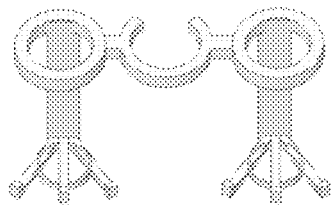
FIG. 5B shows a front perspective view with the attachment member as a ring with a cutout opening, solid arms, and restraints, each as a holster, that is, a restraint upper ring and a restraint lower base connected by a perpendicular stem, in accordance with another embodiment.
Figure 5C:
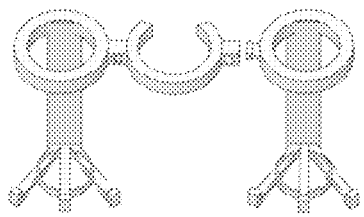
FIG. 5C shows a front perspective view with the attachment member as a ring with a cutout opening, arms with the ability to detach and interlock, and restraints, each as a holster, that is, a restraint upper ring and a restraint lower base connected by a perpendicular stem, in accordance with another embodiment.
Figure 5D:
FIG. 5D shows a perspective view with the attachment member as a ring with a cutout opening, arms with the ability to detach and interlock, and restraints as rings with cutout openings, in accordance with one embodiment.
Figure 5E:
FIG. 5E shows a perspective view with the attachment member as a fully-enclosed ring, solid arms, and restraints as rings with cutout openings, in accordance with one embodiment.
Figure 5F:
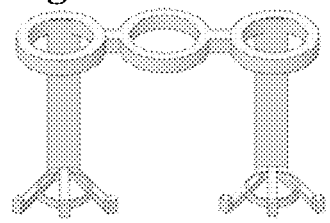
FIG. 5F shows a front perspective view with the attachment member as a fully-enclosed ring, solid arms, and restraints, each as a holster, that is, a restraint upper ring and a restraint lower base connected by a perpendicular stem, in accordance with another embodiment.
Figure 5G:
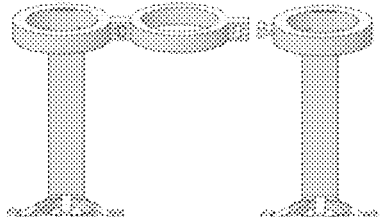
FIG. 5G shows a front perspective view, with the attachment member as a fully-enclosed ring, arms with the ability to detach and interlock, and restraints, each as a holster, that is, a restraint upper ring and a restraint lower base connected by a perpendicular stem, in accordance with another embodiment.
Figure 5H:
FIG. 5H shows a perspective view with the attachment member as a fully-enclosed ring, arms with the ability to detach and interlock, and restraints as rings with cutout openings, in accordance with another embodiment.
Figure 5I:
FIG. 5I shows a perspective view with the attachment member as an openable ring, an adjustable ring, or an openable and adjustable ring, solid arms, and restraints as rings with cutout openings, in accordance with one embodiment.
Figure 5J:
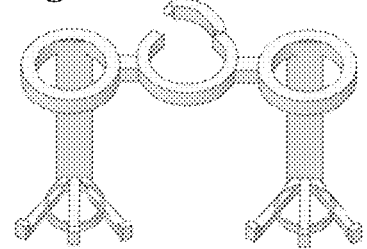
FIG. 5J shows a front perspective view with the attachment member as an openable ring, an adjustable ring, or an openable and adjustable ring, solid arms, and restraints, each as a holster, that is, a restraint upper ring and a restraint lower base connected by a perpendicular stem, in accordance with another embodiment.
Figure 5K:
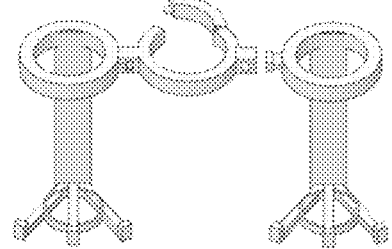
FIG. 5K shows a front perspective view with the attachment member as an openable ring, an adjustable ring, or an openable and adjustable ring, arms with the ability to detach and interlock, and restraints, each as a holster, that is, a restraint upper ring and a restraint lower base connected by a perpendicular stem, in accordance with another embodiment.
Figure 5L:
FIG. 5L shows a perspective view with the attachment member as an openable ring, an adjustable ring, or an openable and adjustable ring, arms with the ability to detach and interlock, and restraints as rings with cutout openings, in accordance with another embodiment.
Figure 5M:
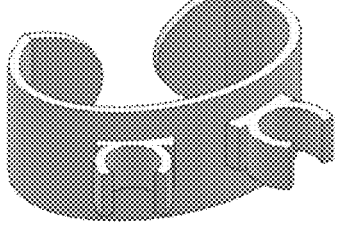
FIG. 5M shows a perspective view with the attachment member as an open band, solid arms, and restraints as cutout rings, in accordance with another embodiment.
Figure 5N:
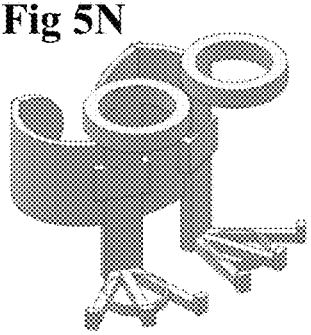
FIG. 5N shows a perspective view with the attachment member as an open band, solid arms, and restraints, each as a holster, that is, a restraint upper ring and a restraint lower base connected by a perpendicular stem, in accordance with another embodiment.
Figure 5O:
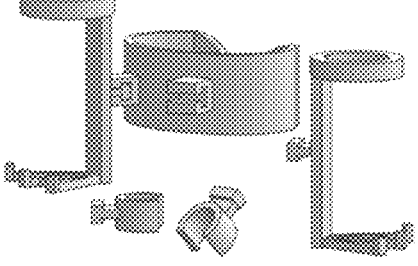
FIG. 5O shows a perspective view with the attachment member as an open band, arms with the ability to detach and interlock, and restraints as cutout rings or each as a holster, that is, a restraint upper ring and a restraint lower base connected by a perpendicular stem, or a combination thereof, in accordance with another embodiment.
Figure 5P:
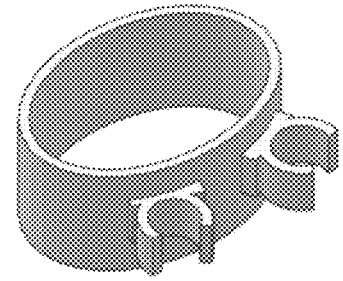
FIG. 5P shows a perspective view with the attachment member as a fully-enclosed band, solid arms, and restraints as cutout rings, in accordance with another embodiment.
Figure 5Q:
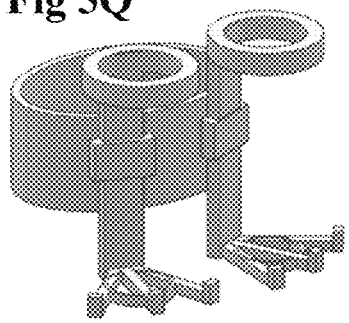
FIG. 5Q shows a perspective view with the attachment member as a fully-enclosed band, solid arms, and restraints as holsters, that is, an upper restraint and a lower parallel restraint connected by a perpendicular stem, in accordance with another embodiment.
Figure 5R:
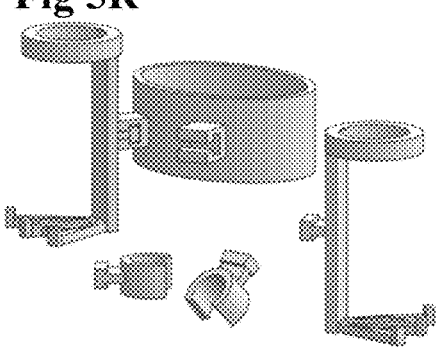
FIG. 5R shows a perspective view with the attachment member as a fully-enclosed band, arms with the ability to detach and interlock, and restraints as cutout rings or holsters, that is, a restraint upper ring and a restraint lower base connected by a perpendicular stem, or a combination thereof, in accordance with another embodiment.

Description—Additional Embodiment (FIGS. 5A-R):

Additional embodiments are shown in FIGS. 5A-R.

FIGS. 5A-D show embodiments with the attachment member as a ring with a cutout opening. FIGS. 5E-H show embodiments with the attachment member as a fully-enclosed ring. FIGS. 5I-L show embodiments with the attachment member as an openable ring, an adjustable ring, or an openable and adjustable ring. FIGS. 5M-O show embodiments with the attachment member as an open band attachment member. FIGS. 5P-R show embodiments with the attachment member as a fully-enclosed band. FIGS. 5A, 5D, 5E, 5H, 5I, 5L, 5M, and 5P show embodiments with restraints as cutout rings. FIGS. 5B, 5C, 5F, 5G, 5J, 5K, 5N, 5O, 5Q, and 5R show embodiments with restraints as holsters. FIGS. 5A, 5B, 5E, 5F, 5I, 5J, 5M, and 5P show embodiments with solid arms. FIGS. 5C, 5D, 5G, 5H, 5K, 5L, 5O, and 5R show embodiments with arms with the ability to detach and interlock; the interlocking arms enable the user to switch out the restraint mechanism to be any combination of cutout ring restraints and holster restraints.

Description-Additional Embodiment (FIG. 6):

FIG. 6 shows an additional embodiment. A plurality of restraints extend a short direct attachment arm 612 sufficient for applying means for joining to the bottle. The plurality of restraints may be cutout ring restraints 114, holster restraints 208, or a combination of cutout ring restraints 114 and holster restraints 208.

Means for joining to the bottle may include adhesive. Additionally, the size of the restraints may allow for the elimination of the attachment arms and thus, the restraints would be joined directly to the bottle.

Operation—Additional Embodiment (FIG. 6):

The means for joining the restraints to the bottle is applied to the bottle, then the restraints are applied to the means for joining. These steps can be done in any order.

Conclusion, Ramifications, and Scope

Thus, the reader will see that at least one embodiment of the syringe and plunger clip provides a more hygienic and convenient, yet economical device that can be used by persons of almost any age and for any kind of liquid medicine recipient: infants, the disabled, the elderly, and animals, to name a few. Alternatively, some embodiments could be utilized for non-medicine purposes such as crafting, mechanics, woodworking, or other fields where it is desirable to secure multiple cylindrical items to another item.

While my above description contains many specificities, these should not be construed as limitations on the scope, but rather as an exemplification of several embodiments thereof. Many other variations are possible. Any material such as plastic, silicone, rubber, wood, or metal would be suitable. The elements may be intrinsically joined together or formed separately and joined with adhesive, hardware connections such as screws or nails, welding or soldering metal components, or another suitable method. Additionally, the entire clip could be much larger or smaller in size to accommodate bottles, syringes, and separated plungers of various sizes. The attachment mechanism, the restraints, and the joining arms could be various shapes. For example, the restraints could be comprised of bucket-shapes for the syringe and separated plunger to rest in, the arms could be triangles, and/or the restraints could be squares or hexagons. The restraint lower base could present with any number of sufficient draining designs. The device could be tagged or written on or may be partially made of dry erase material, thus enabling explicit identification of the correct medicine recipient. The clip could have any of the arm and/or attachment ring embodiments in any permutation. Accordingly, the scope should be determined not by the embodiments illustrated, but by the appended claims and their legal equivalents.

What is claimed is:

1. A drying and storage assembly to releasably secure a separated cylindrical syringe and cylindrical plunger to a medicine bottle, said assembly comprising:
   a member attachable to a neck of the bottle, and rest on a shoulder of the bottle, wherein said neck of the bottle comprises a first diameter and extends to said shoulder of the bottle comprising a second larger diameter, and said member rests on said shoulder of the bottle, such that said member and rests an entire weight of said assembly on said shoulder of the bottle;
   a plurality of restraints to receive releasably said syringe and said plunger respectively, said restraints comprising c-shaped clamps, enabling said separated cylindrical syringe and said cylindrical plunger to snap into said restraints and be snugly and releasably secured, said assembly serving to lift said cylindrical syringe and said cylindrical plunger above a lower surface upon which said bottle rests; and
   a plurality of arms being coupled to and extending from said member for joining said restraints to said member;
   wherein said plurality of arms maintain balance of said drying and storage assembly when attached to said bottle, regardless of a first weight of said bottle and a second weight of contents of said bottle, to enable said bottle to sit upright on said lower surface, by using a combination of the diverging directionality of said plurality of arms and the weight-bearing juncture of said drying and storage assembly and said bottle to overcome potential instabilities in weight distribution created by at least one of said bottle being smaller, said bottle consisting of lightweight materials, and said second weight of contents of said bottle consisting of a smaller quantity or being empty entirely.

2. The assembly of claim 1 wherein said plurality of arms comprises a plurality of interlocking arms, each of the plurality of interlocking arms joins a respective one of said restraints to said member.

3. The assembly of claim 1 wherein said assembly is comprised of at least one of plastic, silicone, wood, and metal.

4. The assembly of claim 1 wherein said member is attachable to said bottle via at least one of an openable mechanism, an adjustable mechanism, and an openable and adjustable mechanism.

5. The assembly of claim 1 wherein said member is a fully-enclosed ring that slideably connects to said bottle by being lowered over a cap of said bottle and resting on said shoulder of the bottle.

6. A method for attaching a separated syringe and plunger to a medicine bottle for drying and storage comprising:
   attaching a member to a neck of the bottle wherein said member both attaches to a first diameter of said neck of said bottle and also rests a weight of said member on a second larger diameter of a shoulder of the bottle which extends from said neck of the bottle, said member coupled to a plurality of arms each of which extend to one of a plurality of drying and holding structures, wherein said plurality of arms rest on said shoulder and balance said weight of said member and said plurality of drying and holding structures on said bottle and enable said bottle to sit upright on a lower surface with said member and said separated syringe and plunger attached; and
   releasably securing said separated syringe to a first drying and holding structure of said plurality of said drying and holding structures; and
   releasably securing said plunger to a second drying and holding structure of said plurality of drying and holding structures;
   wherein said plurality of arms balance said member, said plurality of arms, and said plurality of drying and holding structures upon said bottle in conjunction with the weight-bearing juncture of said member by extending from said member at a sufficient directional degree to enable weight distribution for said bottle to sit upright on a lower surface, overcoming potential instabilities in weight distribution created by at least one of said bottle being smaller, said bottle consisting of lightweight materials, and said second weight of contents of said bottle consisting of a smaller quantity or being empty entirely.

7. The method of claim 6 further comprising detaching said member by exerting gentle opposing directional force simultaneously on said bottle and said member to release said member from said bottle.

8. The method of claim 6 further comprising detaching said separated syringe by pulling said separated syringe from one of said drying and holding structures while holding one of said drying and holding structures securely.

9. The method of claim 6 further comprising detaching said plunger by pulling said plunger from one of said drying and holding structures while holding one of said drying and holding structures securely.

* * * * *